United States Patent
Wang et al.

(10) Patent No.: US 10,209,794 B2
(45) Date of Patent: Feb. 19, 2019

(54) DEVICE FOR TOUCH-SENDING FUNCTIONS, DISPLAY PANEL CONTAINING THE SAME, AND METHOD FOR OPERATING THE SAME

(71) Applicant: BOE TECHNOLOGY GROUP CO., LTD., Beijing (CN)

(72) Inventors: Xuefei Wang, Beijing (CN); Xiangxiang Zou, Beijing (CN); Tieshi Wang, Beijing (CN); Wanpeng Teng, Beijing (CN); Yan Wei, Beijing (CN); Chunfang Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 67 days.

(21) Appl. No.: 15/304,763

(22) PCT Filed: Sep. 18, 2015

(86) PCT No.: PCT/CN2015/090016
§ 371 (c)(1),
(2) Date: Oct. 17, 2016

(87) PCT Pub. No.: WO2017/045203
PCT Pub. Date: Mar. 23, 2017

(65) Prior Publication Data
US 2017/0269723 A1    Sep. 21, 2017

(51) Int. Cl.
*A61B 5/1455* (2006.01)
*G06F 3/041* (2006.01)
*A61B 5/11* (2006.01)
*A61B 5/00* (2006.01)

(52) U.S. Cl.
CPC ........... *G06F 3/041* (2013.01); *A61B 5/1126* (2013.01); *A61B 5/14551* (2013.01);
(Continued)

(58) Field of Classification Search
CPC ........... G06F 3/041; G06F 2203/04105; A61B 5/0205; A61B 5/1455; A61B 5/14551;
(Continued)

(56) References Cited

U.S. PATENT DOCUMENTS

2006/0211925 A1* 9/2006 Lamego ............. A61B 5/14552
600/310
2015/0062078 A1 3/2015 Christman et al.
(Continued)

FOREIGN PATENT DOCUMENTS

CN     103135876 A    6/2013
CN     104346050 A    2/2015
(Continued)

OTHER PUBLICATIONS

State Intellectual Property Office of the P.R.C (SIPO) Office Action 1 for 201580000898.5 Dec. 4, 2017 22 Pages (including translation).
(Continued)

*Primary Examiner* — Eric Winakur
*Assistant Examiner* — Chu Chuan (JJ) Liu
(74) *Attorney, Agent, or Firm* — Anova Law Group, PLLC

(57) ABSTRACT

The present disclosure provides a device for touch-sensing. The device includes a touch surface configured to receive a touch by an object; a measuring portion configured to measure a blood oxygen level of the object; and a control portion configured to calculate a level of pressing force corresponding to the blood oxygen level.

12 Claims, 2 Drawing Sheets

(52) U.S. Cl.
CPC .......... *A61B 5/7435* (2013.01); *A61B 5/6826* (2013.01); *G06F 2203/04105* (2013.01)

(58) Field of Classification Search
CPC .... A61B 5/6826; A61B 5/1126; A61B 5/7435
See application file for complete search history.

(56) References Cited

U.S. PATENT DOCUMENTS

| | | |
|---|---|---|
| 2015/0253334 A1 | 9/2015 | Johnson et al. |
| 2015/0335293 A1* | 11/2015 | Christman ........... A61B 5/6897 600/324 |
| 2017/0153761 A1 | 6/2017 | Park |

FOREIGN PATENT DOCUMENTS

| | | |
|---|---|---|
| CN | 104423767 A | 3/2015 |
| CN | 104579285 A | 4/2015 |
| CN | 104751115 A | 7/2015 |
| CN | 104793806 | 7/2015 |
| CN | 104850821 A | 8/2015 |
| WO | 2015077733 A1 | 5/2015 |

OTHER PUBLICATIONS

The World Intellectual Property Organization (WIPO) International Search Report for PCT/CN2015/090016 dated May 27, 2016 pp. 1-5.

* cited by examiner

DEVICE FOR TOUCH-SENDING FUNCTIONS, DISPLAY PANEL CONTAINING THE SAME, AND METHOD FOR OPERATING THE SAME

This application is a national phase entry under 35 U.S.C. § 371 of International Application No. PCT/CN2015/090016, filed on Sep. 18, 2015. The above enumerated patent application is incorporated by reference herein in its entirety.

FIELD OF THE INVENTION

The present invention generally relates to display technologies and, more particularly, relates to a device for touch-sensing functions, a display panel containing the same, and the method for operating the same.

BACKGROUND

Display panels capable of touch-sensing functions have been widely used in display apparatus such as laptops, tablets, cell phones, and other interfaces between users and computers. In conventional touch-sensing devices, the user often touches the screen of the device to select desired options or to initiate various functions and the device respond to the user based on the touch motions. Conventional devices for blood oxygen measurement are not able to detect and/or respond to different pressing forces applied on the devices.

BRIEF SUMMARY OF THE DISCLOSURE

The present disclosure provides a touch-sensing device capable of measuring changes in the pressing force based on changes in the blood oxygen level and a method for operating the device. By using the touch-sensing device and the method, the measured blood oxygen level can be used for determining finger pressing force levels and other related functions.

One aspect of the present disclosure includes a device for touch-sensing functions. The device includes a touch surface configured to receive a touch motion by an object; a measuring portion configured to measure a blood oxygen level of the object; and a control portion configured to calculate a level of pressing force corresponding to the blood oxygen level.

Optionally, the device further including a frame configured to package the measuring portion and the control portion.

Optionally, the device further includes a display panel packaged by the frame.

Optionally, the control portion is configured to store at least one blood oxygen level range.

Optionally, at least one blood oxygen level range corresponds to the pressing force level.

Optionally, the control portion is further configured to map one pressing force level to one function.

Optionally, the device further includes a light emitting portion configured to emit light of a plurality of colors; and a light measuring portion configured to measure light reflected by the object.

Optionally, the touch surface is substantially transparent to the plurality of colors.

Optionally, the light emitting portion emits red light and infrared light.

Another aspect of the present disclosure includes a method for operating a device for touch-sensing functions. The method includes receiving a touch motion on a portion of the device for touch-sensing functions by an object; receiving a reading of light of a plurality of colors reflected by the object; determining a blood oxygen level of the object based on light reflected by the object; and determining a level of pressing force applied by the object based on the blood oxygen level.

Optionally, the method further includes executing a function based on the level of pressing force.

Optionally, the blood oxygen level falls into a blood oxygen level range.

Optionally, the blood oxygen level range corresponds to the level of pressing force.

Optionally, a pressing force level corresponds to a function.

Optionally, the reading of a red light and a reading of an infrared light are reflected by the object for operating the device for touch-sensing functions.

Another aspect of the present disclosure provides a display device, incorporating the disclosed device for touch-sensing functions.

Optionally, the touch surface of the device for touch-sensing functions is a part of a display surface of the display device.

Optionally, the touch surface of the device for touch-sensing functions is not a part of a display surface of the display device.

Optionally, a display surface of the display panel has touch-sensing functions.

Other aspects of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

For those skilled in the art to better understand the technical solution of the invention, reference will now be made in detail to exemplary embodiments of the invention, which are illustrated in the accompanying drawings. Wherever possible, the same reference numbers will be used throughout the drawings to refer to the same or like parts.

When a user presses down his or her finger on a hard surface, the blood oxygen level in the finger tip changes. Generally, the harder the user presses down on a finger, the lower the blood oxygen level is in that finger. In embodiments of the present disclosure, by measuring the blood oxygen levels of a body part, a processing unit may be programmed to determine the pressing forces applied by that body part. Further, once the processing unit determines the level of pressing force, it may trigger various functions based on the level of pressing force. That is, the device provided by the present disclosure may be able to respond to the touch motions and measure and/or respond to different pressing forces applied by the finger based on the different the blood oxygen levels.

One aspect of the present disclosure provides a touch-sensing device.

Figure 1:
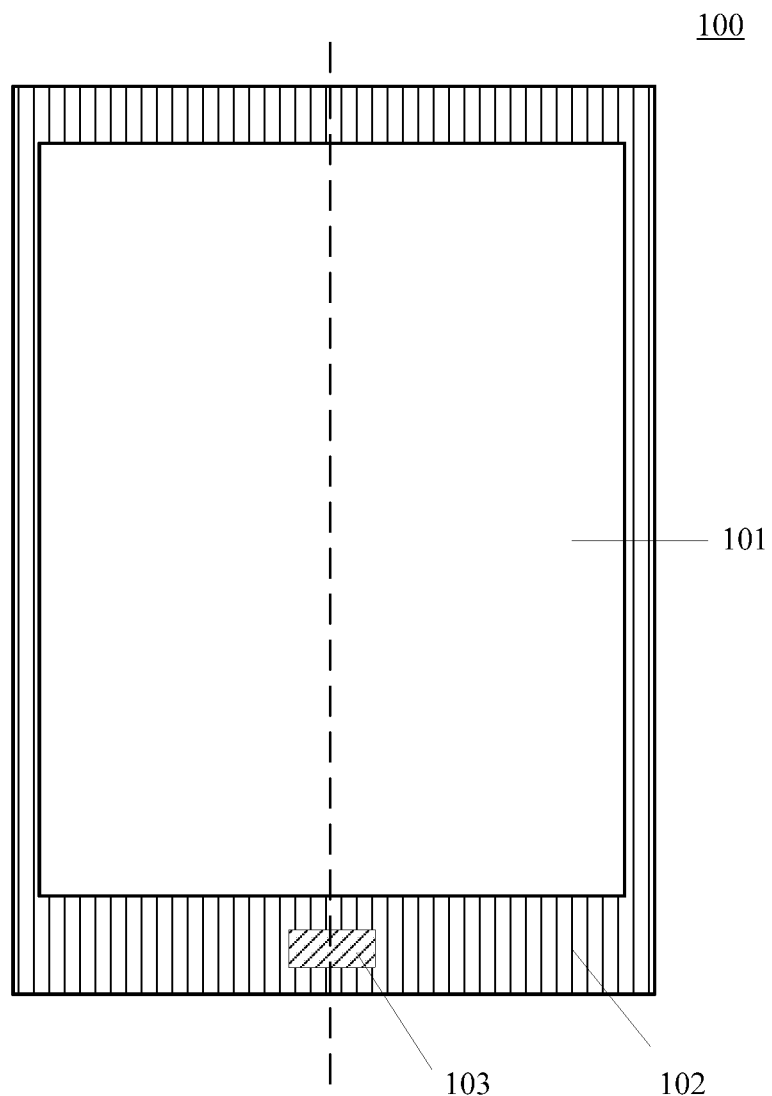
FIG. 1 illustrates a top view of an exemplary touch-sensing device according to the embodiments of the present disclosure.

FIG. 1 shows the top view of the touch-sensing device 100. The device 100 may incorporate functions such as touch-sensing, blood oxygen level measuring, and finger force measuring. The top surface of the device may be a front frame 102 with a Home key region 103. The front frame 102 may cover an active area (AA) region 101. As shown in FIG. 1, the front frame 102 may fully enclose or surround the AA region 101. The Home key region 103 may be a portion of the front frame 102. The area of the Home key region 103 may not overlap with the area of the AA region 101 and may be used for different applications and designs.

The front surface of the touch-sensing device 100, i.e., the front frame 102, and the Home key region 103, may be touch-sensing enabled. The front frame 102 may be used for surrounding or enclosing the AA region 101 and responding to touch motions. The Home key region 103 may be used for responding to certain touch motions and sensing the blood oxygen level of the user. The AA region 101 may be used for responding to touch motions and displaying images. For example, the AA region 101 may be used to display the result of the blood oxygen measurement and the force applied by the touch motion. The AA region 101 may also be used to display other contents. In addition, when a user touches the front frame 102 outside of the Home key region 103, the front frame region 102 may sense the touch motion and send signals reflecting the touch motion on the AA region 101. The AA region 101 may respond to the signals accordingly.

In one embodiment, the Home key region 103 may be substantially transparent to the wavelengths used for sensing the blood oxygen level. For example, in one embodiment, red light of wavelength about 660 nm and infrared light of wavelength about 940 nm may be used to sense the blood oxygen level. The Home key region 103 may thus be substantially transparent to the red light and the infrared light such that the red light and the infrared light emitted from the light sources under the Home key region 103 may be transmitted to the finger pressing the Home key region 103 without significant loss of light intensity. The red light and the infrared light may be absorbed and further reflected back to a receiver under the Home key region 103 to be collected. Because the absorption coefficient of red light and infrared light by human blood and human tissues are stable, based on certain ratios of absorbed red light and absorbed infrared light, the blood oxygen level of the user can be measured. The collected light may be used for calculating the blood oxygen level of the finger. In addition to being substantially transparent to the wavelengths used for sensing, the Home key region 103 may also be sufficiently transparent to light of other wavelengths such as visible light. It should be noted that, according to different applications, light of different wavelengths or colors, e.g., green light, may be used for the measurement of the blood oxygen level. The specific colors of the light and the numbers of different colors of light used in the device should not be limited to the embodiments herein.

The front surface of the touch-sensing device, i.e., the AA region 101, the front frame region 102, and the Home key region 103, may be made of glass or other suitable transparent materials. Certain light-emitting layer such as an organic light-emitting diode (OLED) layer or a liquid crystal display (LCD) layer may be formed under the AA region for displaying images. The light-emitting layer may also be incorporated with touch-sensing components or design to facilitate touch-sensing functions. Certain circuits or designs may be incorporated under the front frame region 102 and the Home key region 103 to facilitate touch-sensing functions.

Figure 2:
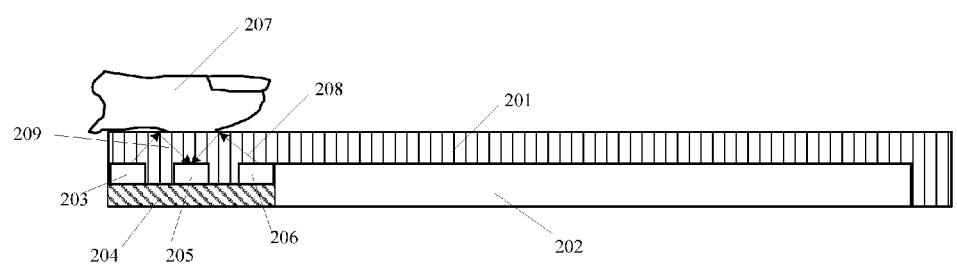
FIG. 2 illustrates a cross-section view of the touch-sensing device according to the embodiments of the present disclosure.

FIG. 2 illustrates a cross-section view of the touch-sensing device with a human finger pressing on the Home key region.

As shown in FIG. 2, the touch-sensing device may include a front frame 201, a display panel 202, a first light-emitting module 203, a printed circuit board (PCB) 204, a receiver 205, a second light-emitting module 206, and a control unit (not shown). The display panel 202 may be aligned with the PCB 204 horizontally. The first light-emitting module 203, the second light-emitting module 206, and the receiver 205 may be mounted on the PCB 204. The front frame 201 may fully cover the display panel 202, the first light-emitting module 203, the second light-emitting module 206, and the receiver 205. The control unit may be arranged in any suitable position within the touch-sensing device and connected to at least the receiver 205, the display panel 202, and the front frame 201.

The front surface of the first light-emitting module 203, the front surface of the second light-emitting module 206, and the front surface of the receiver 205 may be horizontally coplanar. The receiver 205 may be mounted between the first light-emitting module 203 and the second light-emitting module 206. Light emitted by the first light-emitting module 203 or the second light-emitting module 206 and propagated towards the Home key region may be represented by the arrows 208, and light received by the receiver 205 from the Home key region may be represented by the arrow 209. For illustrative purposes, the arrows may only represent the directions of the light transmitted for the blood oxygen measurements and do not reflect the actual transmission of the light emitted by the light-emitting modules.

In operation, light emitted by the first light-emitting module 203 and the second light-emitting module 206, not transmitted to the finger 207 pressing the Home key region, may be reflected by the front surface of the front frame 201 and received by the receiver 205. Also, light emitted by the first light-emitting module 203 and the second light-emitting module 206, transmitted to the finger 207 pressing the Home key and partially absorbed by the finger 207, may also be reflected back and received by the receiver 205. In one embodiment, the receiver 205 may be placed in the middle of the first light-emitting module 203 and the second light-emitting module 206.

The receiver 205 may further send information or signals reflecting the received reflected light to the control unit. The control unit may be used to sense and respond to touch motions. The control unit may further be used to store information such as the power or intensity of light emitted by the first light-emitting module 203 and the second light-emitting module 206, and certain algorithms to calculate the pressing force level of the finger 207 based on the reflected light. The control unit may further be used to store commands corresponding to different blood oxygen levels or pressing force levels. By comparing the power or intensity of the emitted light and the received light through suitable algorithms, the control unit may perform various calculations on the light absorbed by the finger 207. The information of absorbed light may be used to determine the blood oxygen level of the finger 207. The control unit may further determine the pressing force level applied by the finger 207 using the obtained blood oxygen level. For example, a higher blood oxygen level may correspond to a lower intensity of pressing force level, and a lower blood oxygen level may correspond to a higher intensity of pressing force level.

The measured intensity of the pressing force level may or may not be displayed on the display panel 202. In one embodiment, the pressing force level may be displayed on the display panel 202. In various other embodiments, the pressing force level may not be displayed on the display panel 202 and may be used for initiating further actions of the touch-sensing device. For example, a lower pressing force level may correspond to one command stored in the control unit, and a higher pressing force level may correspond to another command stored in the control unit. The commands may correspond to various actions of the touch-sensing device such as turning off the touch-sensing device, opening a certain application, or other suitable functions can be performed by touch-sensing device. The data and instructions to initiate various functions based on pressing force levels may be stored in the control unit.

The control unit may be a processing unit used to control various functions of the touch-sensing functions. The control unit may include a processor, a random access memory (RAM) unit, a read-only memory (ROM) unit, a storage unit, a display, an input/output interface unit, a database, and a communication interface. Other components may be added and certain devices may be removed without departing from the principles of the disclosed embodiments.

In operation, when a human finger 207 is placed on the Home key region, the touch motion may be sensed by the front frame 201 and the control unit, and the first light-emitting module 203 and the second light-emitting module 206 may start emitting light in response to the touch motion or corresponding commands from the control unit. The reflected light may be received by the receiver 205, and blood oxygen level of the finger can be calculated by the control unit. Further, the obtained blood oxygen level may be used to calculate the pressing force level, and the pressing force level may also be used for other functions. The operation may be automatic. That is, when a human finger is placed on the Home key region, depending on the pressing force levels, the touch-sensing device may be perform different actions.

It should be noted that, the touch-sensing device may also include other functions. The functions may or may not be combined with the blood oxygen measurement and the pressing force level measurement. For example, the touch-sensing device may further include a fingerprint scanning function. The finger scanning function may be combined with the blood oxygen measurement to distinguish a living body from a non-living body. Other suitable functions may also be implemented in the touch-sensing device to be combined with the blood oxygen or pressing force level measurement.

In certain embodiments, the first light-emitting module 203 and the second light emitting-module 206 may emit light constantly regardless of a touch motion. In this case, when the user places a finger on the Home key region, the touch-sensing device may also automatically measure the blood oxygen level and the pressing force level. Working principles of the measuring process are aforementioned and not repeated herein.

The first light-emitting module 203 and the second light-emitting module 206 may be any suitable light-emitting devices capable of emitting wavelengths for blood oxygen measurement. In one embodiment, the wavelengths for the blood oxygen measurement may be red and infrared. That is, one of the first light-emitting module 203 and the second light-emitting module 206 may emit red light, and the other may emit infrared light. The receiver 205 may be any photoelectric device capable of converting light signals into electric current signals. In one embodiment, the first light-emitting module 203 and the second light-emitting module 206 may both be light-emitting diodes (LEDs), and the receiver 205 may be a photodiode.

The display panel 202 may be any suitable device capable of display images and respond to touch motions. The display panel 202 may or may not be combined with the front frame 201 to sense and respond to touch motions. That is, the touch surface of the touch-sensing device may or may not be a part of a display surface of the display panel 202. The working principles of the display panel 202 and the front frame 201 may be referred to any blood oxygen measuring devices and are not repeated herein.

Thus, using the disclosed touch-sensing device, pressing force level may be determined based on the blood oxygen level of the finger. The pressing force level may also be used for further actions or be combined with certain other functions of the touch-sensing device. By varying the pressing force levels, the user may be able to control the touch-sensing device to perform different functions or switch between different tasks. The touch-sensing device may be more efficiently used.

Another aspect of the present disclosure provides a method for operating the touch-sensing device.

Figure 3:
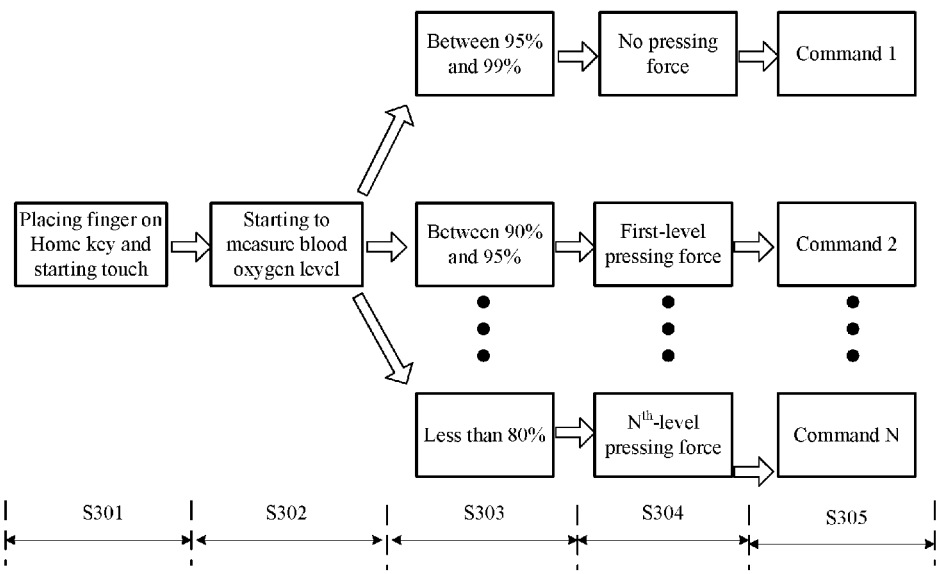
FIG. 3 illustrates an exemplary process for operating the touch-sensing device according to the embodiments of the present disclosure.

FIG. 3 illustrates an exemplary operation process of the touch-sensing device. The operation process may include steps S301 to S305.

In step S301, the user may place the finger on the Home key region of the touch-sensing device and press the Home key region with a desired pressing force level.

The pressing force level may be any suitable pressing force level capable of controlling the touch-sensing device to perform certain functions. For example, the user may press the Home key region with a high pressing force to subsequently turn off the touch-sensing device. That is, the high pressing force level applied on the Home key region may correspond to a "turn off" function of the touch-sensing device. Also, the user may apply little or no force on the Home key region so that the touch-sensing device may measure the blood oxygen level and the corresponding pressing force level, i.e., little or no force, and keep previous actions. That is, a low pressing force level may correspond to a "maintaining same status" function of the touch-sensing device. The specific functions may be programmed according to different applications or designs and are thus not limited by the disclosed embodiments.

In step S302, the touch-sensing device may start measuring the blood oxygen level.

The front frame of the touch-sensing device may sense the touch motion and the light reflected by the finger after absorption may be received by the receiver. The receiver may send data or signals indicative of the reflected light to the control unit such that the control unit may compare the intensity of the reflected light with previously stored intensity of the light emitted by the light-emitting modules to determine the portion of light absorbed by the human finger. Details of the working principles may be aforementioned and are thus not repeated here.

In step S303, the control unit may be used to calculate the blood oxygen level and determine the range of pressing force levels.

The portion of light absorbed by the finger may be applied in certain algorithms by the control unit to calculate blood oxygen level of the finger. For example, the control unit may be used to store previously determined blood oxygen level ranges such as 95% to 99%, 90% to 95%, and so on. The ranges may be defined to include all levels of pressing force levels. For example, a blood oxygen level of 95% to 99% may map to pressing force level 0 or the $0^{th}$ level; a blood oxygen level of 90% to 95% may map to pressing force level 1 or the $1^{st}$ level, etc. The specific level defined by each range may be set according to different applications and is not limited by the embodiments disclosed herein.

In step S304, the control unit may be used to determine the pressing force level corresponding to the blood oxygen level.

The control unit may contain previously-stored relationship between a certain blood oxygen level and the corresponding pressing force level. Each range of blood oxygen levels may correspond to a certain pressing force level. The control unit may determine the corresponding pressing force level of the blood oxygen level based on the range the measured blood oxygen level falls in. For example, if the blood oxygen level is between 95% and 99%, the control unit may determine no pressing force level is applied on the Home key region by the finger. If the blood oxygen level is between 90% and 95%, the control unit may determine a first-level (e.g., moderate) pressing force is applied on the Home key region by the finger. If the blood oxygen level is less than 80%, the control unit may determine an $N^{th}$-level pressing force (high force) is applied on the Home key region by the finger. Various algorithm and criteria previously stored in the control unit may be applied by the control unit to calculate the pressing force level based on the blood oxygen level. In certain embodiments, the heart rate of the user, placing the finger on the Home key region, may be calculated based on the blood oxygen levels. In this case, the relationship between a certain range of blood oxygen level and heart rate may be pre-stored in the control unit. The heart rate may be displayed according to the commands from the user or may be used for other future actions.

In step S305, the control unit may execute the function corresponding to the pressing force level.

Each level of pressing force level may correspond to a function. The control unit may determine the function based on the level of pressing force level. For example, if no pressing force level is applied on the Home key region, the control unit may proceed to or execute function 1. If the first-level pressing force is applied on the Home key region, the control unit may proceed to function 2. If the $N^{th}$-level pressing force is applied on the Home key region, the control unit may proceed to function N.

A function may be any suitable action the touch-sensing is capable of performing such as turning off the touch-sensing device, switching between tasks, showing the calculated heart rate, turning on a certain application, etc. The control unit may also control the display panel to display instructions or options corresponding to the actions so that the user may make selections accordingly.

For example, a user may press the Home key region with certain pressing force level, and the touch-sensing device may sense the touch motion and measure the blood oxygen level of the finger. Further, the control unit may calculate the pressing force level of the finger based on the blood oxygen level. The control unit may further determine the function to execute based on the level of the pressing force level. In an embodiment, blood oxygen level may be measured to be between 90% and 95%. The control unit may determine that the corresponding pressing force level is the first-level pressing force. The control level may then proceed to execute function 2. In this case, function 2 may be a "return to the main menu" instruction. That is, when the user presses the Home key region with the first-level pressing force, the touch-sensing display device may return to the main menu automatically. Similarly, when the user increases or decreases the level or amount of pressing force level applied on the Home key region, the touch-sensing device may switch to another application or display different options on the display panel for the user to choose.

As described above, the functions may be various actions the touch-sensing device is capable of performing. The touch-sensing device may thus incorporate various functions. Certain components or devices may be incorporated into the touch-sensing device to facilitate these functions. By using the method provided by the present disclosure, the blood oxygen level of the user may be measured, and the touch-sensing display device may perform different actions based on the pressing force level applied on the touch-sensing device. The touch-sensing display device may be more efficiently used. Because the touch-sensing display device may also be incorporated in other device to be combined with other functions, fabrication cost can be reduced.

In some embodiments of the present disclosure, the touch-sensing device may be integrated with other touch display technologies. For example, a touch display apparatus may include multiple touch-sensing devices on a large display surface. The touch-sensing devices measure the blood oxygen level change in a body part (e.g., a finger) and then determine the levels of pressing forces as described in relation to FIG. 3. The touch display apparatus may also measure the touch motion using other touch sensing technologies to determine, for example, the location of a touch on the large display surface. A control unit may then trigger various functions based on the determined touch pressing force as well as the location of the touch motion. For example, as shown in the table below, if a user applies a same pressing force at different locations of the display surface, the user action may trigger different functions.

| User Pressing Force | User Pressing Location | Control Program Instruction |
|---|---|---|
| Level 1 | Location A | Function 1 |
| Level 2 | Location A | Function 2 |
| Level 2 | Location B | Function 3 |
| Level 3 | Location B | Function 4 |

In some embodiments of the present disclosure, a touch-sensing device may also combine the measurements of pressing force level with other measurements, such as the time of the press motion. A control unit may then trigger various functions based on the determined touch pressing force as well as the length of time of the touch motion.

Another aspect of the present disclosure provides a display device. The touch-sensing device and the method for operating the touch-sensing device according to the embodiments of the present disclosure can be used in various products with touch-sensing functions. For example, the touch-sensing device may be incorporated in a display device of a smart phone so that the user may control certain functions of the smart phone by touching certain area (e.g., the Home key region) of the smart phone with varying pressing forces. The touch-sensing device may also be incorporated in an LCD device, an OLED device, an electronic paper, a digital photo frame, a mobile phone, a tablet computer, and so on.

It should be understood that the above embodiments disclosed herein are exemplary only and not limiting the scope of this disclosure. Without departing from the spirit and scope of this invention, other modifications, equivalents, or improvements to the disclosed embodiments are obvious to those skilled in the art and are intended to be encompassed within the scope of the present disclosure.

What is claimed is:

1. A device for touch-sensing functions, comprising:
   a touch surface configured to receive a touch by an object;
   an optical sensor; and
   a control unit configured to:
      determine a blood oxygen level of the object based on readings from the optical sensor;
      determine one of a plurality of blood oxygen level ranges within which the blood oxygen level of the object falls;
      determine one of a plurality of pressing force levels that corresponds to the one of the plurality of blood oxygen level ranges according to a mapping relationship between pressing force levels and blood oxygen level ranges;
      determine one of a plurality of commands that corresponds to the one of the plurality of pressing force levels according to a mapping relationship between commands and pressing force levels; and
      control the device for touch-sensing functions to take an action in accordance with the one of the plurality of commands.

2. The device according to claim 1, further including a frame configured to package the control unit.

3. The device according to claim 2, further including a display panel packaged by the frame.

4. The device according to claim 1, wherein the optical sensor comprises: a light emitting device configured to emit light of a plurality of colors; and a receiver configured to measure the red light and the infrared light reflected by the object.

5. The device according to claim 4, wherein the touch surface is substantially transparent to the plurality of colors.

6. The device according to claim 4, wherein the light emitting device emits red light and infrared light.

7. A method for operating a device for touch-sensing functions, comprising:
   receiving a touch motion on a portion of the device for touch-sensing functions by an object;
   receiving a reading of light of a plurality of colors reflected by the object;
   determining a blood oxygen level of the object based on the readings of a red light and an infrared light reflected by the object;
   determining one of a plurality of blood oxygen level ranges within which the blood oxygen level of the object falls;
   determining one of a plurality of pressing force levels that corresponds to the one of the plurality of blood oxygen level ranges according to a mapping relationship between pressing force levels and blood oxygen level ranges;
   determining one of a plurality of commands that corresponds to the one of the plurality of pressing force levels according to a mapping relationship between commands and pressing force levels; and
   controlling the device for touch-sensing functions to take an action in accordance with the one of the plurality of commands.

8. The method according to claim 7, further comprising:
   operating the device for touch-sensing functions by using the readings of the red light and the infrared light reflected by the object.

9. A display device, incorporating the device for touch-sensing functions according to claim 1.

10. The display device according to claim 9, wherein the touch surface of the device for touch-sensing functions is a part of a display surface of the display device.

11. The display device according to claim 9, wherein the touch surface of the device for touch-sensing functions is not a part of a display surface of the display device.

12. The display device according to claim 9, wherein a display surface of the display device has touch-sensing functions.

* * * * *